(12) United States Patent
Gaither (10) Patent No.: US 10,011,926 B2
(45) Date of Patent: Jul. 3, 2018

(54) KNIT SOCK WITH TARGETED COMPRESSION ZONE

(71) Applicant: Flagship Brands, LLC, Conover, NC (US)

(72) Inventor: Hugh Gaither, Newton, NC (US)

(73) Assignee: Flagship Brands, LLC, Hickory, NC (US)

( * ) Notice: Subject to any disclaimer, the term of this patent is extended or adjusted under 35 U.S.C. 154(b) by 0 days.

(21) Appl. No.: 15/716,953

(22) Filed: Sep. 27, 2017

(65) Prior Publication Data

US 2018/0016715 A1 Jan. 18, 2018

Related U.S. Application Data

(63) Continuation of application No. 14/643,677, filed on Mar. 10, 2015, now Pat. No. 9,803,300, which is a continuation of application No. 13/885,022, filed as application No. PCT/US2011/001898 on Nov. 15, 2011, now Pat. No. 8,973,411.

(60) Provisional application No. 61/456,925, filed on Nov. 15, 2010.

(51) Int. Cl.
*D04B 1/26* (2006.01)
*A41B 11/00* (2006.01)
*A61F 13/08* (2006.01)

(52) U.S. Cl.
CPC .............. *D04B 1/26* (2013.01); *A41B 11/003* (2013.01); *A61F 13/08* (2013.01); *A41B 2400/38* (2013.01)

(58) Field of Classification Search
CPC . D04B 1/26; D04B 1/265; D04B 9/52; D04B 9/56; A41B 11/003
See application file for complete search history.

(56) References Cited

U.S. PATENT DOCUMENTS

| | | | |
|---|---|---|---|
| 2,100,861 A | 11/1937 | Lochhead | |
| 2,102,368 A * | 12/1937 | Martel | D04B 1/18 66/182 |
| 2,219,235 A * | 10/1940 | Morton | A41B 11/003 2/239 |
| 2,379,649 A | 7/1945 | Nebel | |
| 3,154,933 A | 11/1964 | Holder | |
| 3,157,037 A | 11/1964 | Nebel et al. | |
| 3,162,029 A | 12/1964 | Laws et al. | |
| 4,015,448 A | 4/1977 | Knohl | |
| 4,034,581 A | 7/1977 | Swafford | |
| 4,194,249 A | 3/1980 | Thorneburg | |
| 4,216,662 A | 8/1980 | Harris, Jr. et al. | |
| 4,253,317 A | 3/1981 | Howard et al. | |

(Continued)

*Primary Examiner* — Danny Worrell
(74) *Attorney, Agent, or Firm* — Schwartz Law Firm, P.C.

(57) ABSTRACT

A knit sock includes a foot portion having an upper instep area and a lower sole area integrally knit of a body yarn in circumferential courses and axial wales. The lower sole area defines inner and outer arch regions. The inner arch region incorporates a targeted compression zone adapted to reside generally adjacent an inner arch of a wearer's foot. The compression zone includes axially extending compression ridges of variable length spaced apart from a top of the compression zone to a bottom of the compression zone. When the sock is worn, a compression force applied by the foot portion within the targeted compression zone is greater than the compression force in directly adjacent areas of said foot portion.

13 Claims, 9 Drawing Sheets

(56) References Cited

U.S. PATENT DOCUMENTS

| | | | |
|---|---|---|---|
| 4,255,949 A * | 3/1981 | Thorneburg | A41B 11/00 |
| | | | 2/239 |
| 4,277,959 A * | 7/1981 | Thorneburg | A41B 11/02 |
| | | | 2/239 |
| 4,494,388 A | 1/1985 | Lau et al. | |
| 4,522,044 A * | 6/1985 | Lineberry | A41B 11/02 |
| | | | 66/172 E |
| 4,589,267 A | 5/1986 | Barbee | |
| 4,732,015 A | 3/1988 | Abrams et al. | |
| 5,103,656 A * | 4/1992 | Hanson, II | A41B 11/003 |
| | | | 2/239 |
| 5,115,650 A | 5/1992 | Patrick et al. | |
| 5,184,485 A | 2/1993 | Bini | |
| 5,983,402 A * | 11/1999 | Fincher | A41B 11/002 |
| | | | 2/239 |
| 6,336,227 B1 * | 1/2002 | Liput | A41B 11/003 |
| | | | 2/239 |
| 6,505,485 B1 | 1/2003 | Eiseberg | |
| 6,805,681 B2 * | 10/2004 | Yokoyama | D04B 1/26 |
| | | | 2/239 |
| 7,721,575 B2 | 5/2010 | Yokoyama | |
| 7,757,518 B2 | 7/2010 | Sho et al. | |
| 7,950,071 B2 * | 5/2011 | Jeong | A41B 11/00 |
| | | | 2/239 |
| 7,971,280 B2 * | 7/2011 | Kaneda | A41B 11/02 |
| | | | 2/239 |
| D657,122 S * | 4/2012 | Gaither | D2/980 |
| D657,123 S * | 4/2012 | Gaither | D2/994 |
| 8,424,116 B2 | 4/2013 | Anastsopoulos et al. | |
| 8,495,765 B2 | 7/2013 | Araki et al. | |
| 8,973,411 B2 * | 3/2015 | Gaither | A61F 13/08 |
| | | | 66/182 |
| D752,334 S * | 3/2016 | Easter | D2/980 |
| 9,803,300 B2 * | 10/2017 | Gaither | A61F 13/08 |
| 2006/0085894 A1 | 4/2006 | Yakopson et al. | |
| 2009/0158404 A1 | 6/2009 | Hahn et al. | |

* cited by examiner

KNIT SOCK WITH TARGETED COMPRESSION ZONE

TECHNICAL FIELD AND BACKGROUND OF THE INVENTION

This invention relates generally to knit hosiery, and more particularly to a circularly-knit sock with a targeted compression zone. In various exemplary applications, the compression zone of the present sock may function alone or in combination with other features to "lock" the sock foot in position on the wearer during use. In addition to improved fit and comfort, the present sock may enhance a runner's proprioception, kinesthetic awareness, stamina or endurance, and overall performance.

SUMMARY OF EXEMPLARY EMBODIMENTS

Various exemplary embodiments of the present invention are described below. Use of the term "exemplary" means illustrative or by way of example only, and any reference herein to "the invention" is not intended to restrict or limit the invention to exact features or steps of any one or more of the exemplary embodiments disclosed in the present specification. References to "exemplary embodiment," "one embodiment," "an embodiment," "various embodiments," and the like, may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

It is also noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

According to one exemplary embodiment, the present disclosure comprises a knit sock including a foot portion having an upper instep area and a lower sole area integrally knit of a body yarn in circumferential courses and axial wales. The lower sole area defines inner and outer arch regions. The inner arch region comprises a targeted (predefined) compression zone adapted to reside generally adjacent an inner arch of a wearer's foot. The compression zone comprises axially extending compression ridges of variable length spaced apart from a top of the compression zone to a bottom of the compression zone. When the sock is worn, a compression force applied by the foot portion within the targeted compression zone is greater than the compression force in directly adjacent areas of said foot portion.

The term "targeted compression zone" as used herein refers to a predefined area of the sock which is of greater density than directly adjacent areas, and which is fabricated to apply greater compression force against an arch of the foot.

In this context of the present disclosure, the term "directly adjacent" means a fabric area located or formed beside or surrounded (in whole or in part) by another fabric area without intervening fabric, parts or other structure.

The term "sock" refers broadly herein to any hosiery or other fabric construction designed to cover at least a portion of the wear's foot. The sock may be knit in whole or in part (e.g., using conventional circular knitting machinery), and may be specially designed for a variety of uses including running, cycling, hiking, golf, hunting, and other general athletic and every-day wear. The sock may comprise a footsock, tube sock, calf-high sock, mid-calf or over-the calf sock, crew sock, stocking, stretch or support hosiery, foot sleeve, foot wrap, or the like. The present sock may also be integrally formed with other garments, such as pantyhose.

According to another exemplary embodiment, the targeted compression zone comprises elastic yarns laid-in the body yarn. Alternatively, the compression zone may be separately formed and separately attached (e.g., by sewing) to parts of the sock.

According to another exemplary embodiment, the targeted compression zone is generally semi-circular. The term "semi-circular" is defined broadly herein to mean any shape having a first side which is generally linear and a second side which is generally arcuate. The compression zone may also be formed in a variety of other shapes including, for example, oval, circular, pyramidal, square, and rectangular.

According to another exemplary embodiment, the targeted compression zone comprises a substantially arcuate side extending between opposite ends of the foot portion, and a substantially linear side opposite the arcuate side.

According to another exemplary embodiment, the arcuate side of the compression zone faces a bottom axial centerline of the foot portion (substantially dividing the lower sole area into inside and outside arch regions).

According to another exemplary embodiment, the linear side of the compression zone extends proximate an inside axial centerline of the foot portion (substantially dividing the lower sole area and the upper instep area).

According to another exemplary embodiment, the compression zone comprises a plurality of spaced axial compression ridges. Each compression ridge may be formed by one or more uncut pattern (or accent or other) yarns. The term "uncut" refers to a single length of yarn extending coursewise across each of the axial wales in the compression zone. In other words, a first free end of the uncut yarn may reside outside a first wale of the compression zone, while the opposite free end resides outside the last wale of the compression zone. These uncut yarns may be thicker than the body yarn, and may be integrated into the compression zone in each circumferential course.

According to another exemplary embodiment, the compression ridges taper (become shorter) in axial length from the linear side of the compression zone towards a center of the arcuate side of the compression zone.

According to another exemplary embodiment, the compression zone comprises double covered elastic yarns.

According to another exemplary embodiment, the size of each double covered elastic yarn is greater than 250 denier.

According to another exemplary embodiment, the compression zone has a tighter gauge (or increased stitch density) than directly adjacent areas of the foot portion. The density in the compression zone may be 50%-100% greater than the density in directly adjacent areas of the sock. In one example, the density in the compression zone is about 70% greater than the density in directly adjacent areas of the sock.

According to another exemplary embodiment, the compression zone has a knit structure distinct from directly adjacent areas of the foot portion.

According to another exemplary embodiment, the foot portion further comprises a heel and a toe.

According to another exemplary embodiment, the upper instep area of the foot portion comprises an intermediate flat knit region.

According to another exemplary embodiment, the intermediate flat knit region in the upper instep area comprises mock ribbing.

According to another exemplary embodiment, the upper instep area of the foot portion further comprises first and second mesh knit regions directly adjacent or adjacent (i.e, proximate) opposite sides of the intermediate flat knit region.

According to another exemplary embodiment, the outer arch region of the lower sole area comprises mock ribbing.

In yet another exemplary embodiment, the present disclosure comprises a knit sock with a foot portion having an upper instep area and a lower sole area integrally knit of a body yarn in circumferential courses and axial wales. The lower sole area comprises a generally semi-circular targeted compression zone. A compression force applied by the foot portion within the targeted compression zone is greater than the compression force in directly adjacent areas of the foot portion.

According to another exemplary embodiment, the targeted compression zone has reduced coursewise and walewise stretchability relative to directly adjacent areas of the foot portion.

BRIEF DESCRIPTION OF THE DRAWINGS

Some of the objects of the invention have been set forth above. Other objects and advantages of the invention will appear as the description proceeds when taken in conjunction with the following drawings, in which.

DESCRIPTION OF EXEMPLARY
EMBODIMENTS AND BEST MODE

The present invention is described more fully hereinafter with reference to the accompanying drawings, in which one or more exemplary embodiments of the invention are shown. Like numbers used herein refer to like elements throughout. This invention may, however, be embodied in many different forms and should not be construed as limited to the embodiments set forth herein; rather, these embodiments are provided so that this disclosure will be operative, enabling, and complete. Accordingly, the particular arrangements disclosed are meant to be illustrative only and not limiting as to the scope of the invention, which is to be given the full breadth of the appended claims and any and all equivalents thereof. Moreover, many embodiments, such as adaptations, variations, modifications, and equivalent arrangements, will be implicitly disclosed by the embodiments described herein and fall within the scope of the present invention.

Although specific terms are employed herein, they are used in a generic and descriptive sense only and not for purposes of limitation. Unless otherwise expressly defined herein, such terms are intended to be given their broad ordinary and customary meaning not inconsistent with that applicable in the relevant industry and without restriction to any specific embodiment hereinafter described. As used herein, the article "a" is intended to include one or more items. Where only one item is intended, the term "one", "single", or similar language is used. When used herein to join a list of items, the term "or" denotes at least one of the items, but does not exclude a plurality of items of the list.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterit) is not intended to indicate or imply that the invention has been previously reduced to practice or that any testing has been performed.

Figure 1:
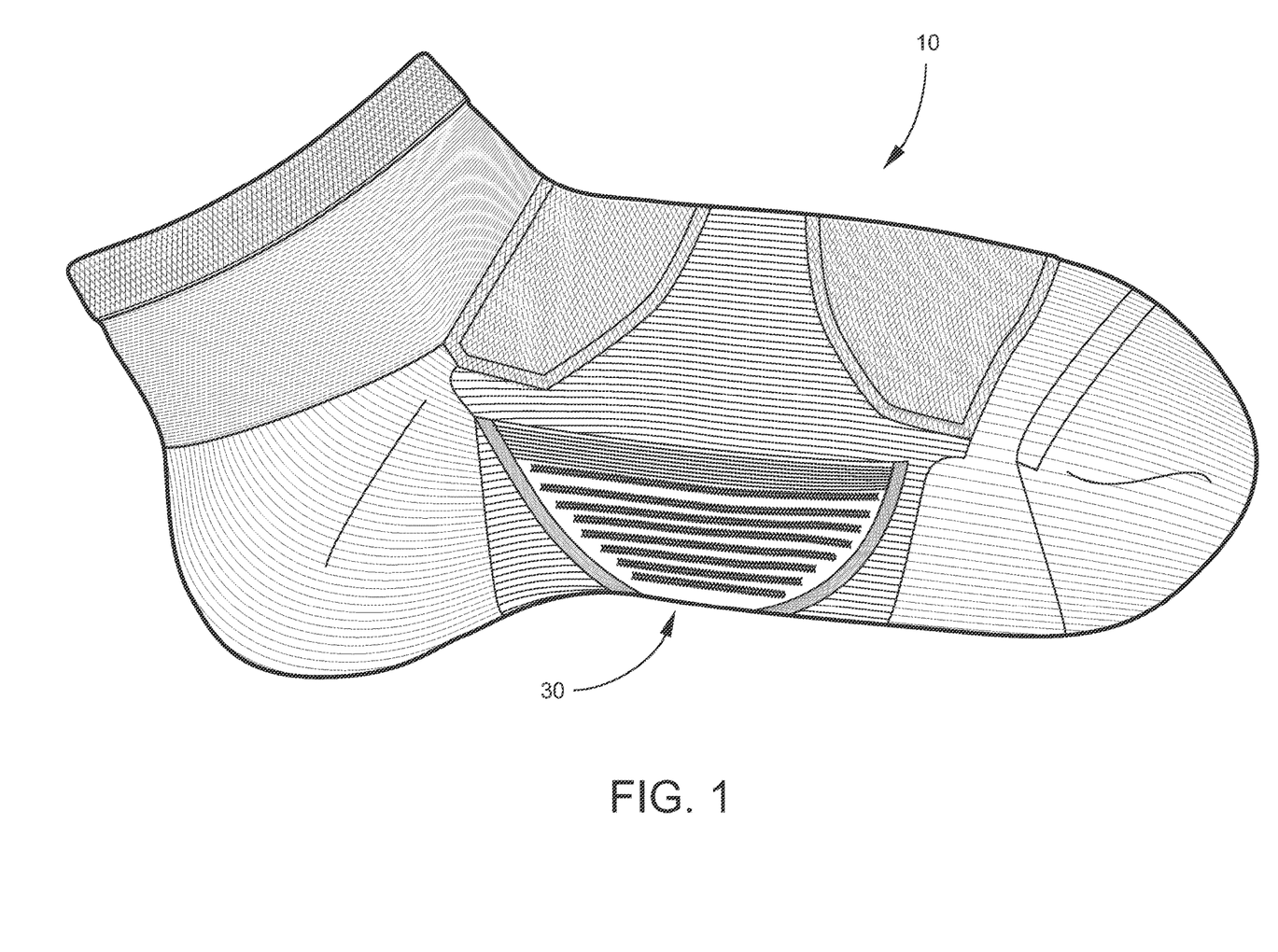
FIG. 1 is a side view of a knit sock incorporating a targeted compression zone according to one exemplary embodiment of the present disclosure.
Figure 2:
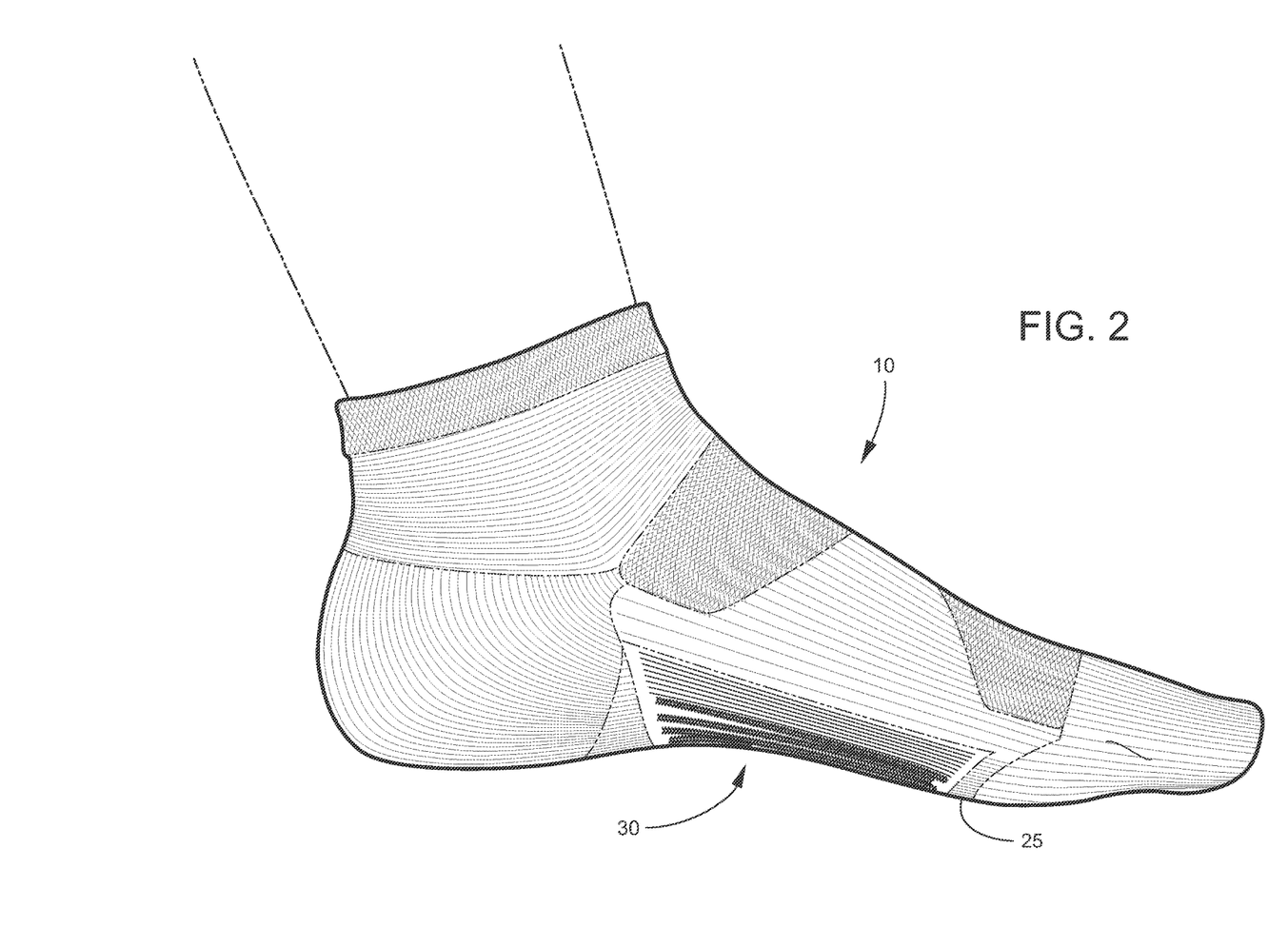
FIG. 2 is a side view of the exemplary sock worn on a foot of wearer, and including surface shading to indicate various areas and regions of distinct knit structure.

Referring now specifically to the drawings, a knit sock according to one exemplary embodiment of the present disclosure is illustrated in FIGS. 1 and 2, and shown generally at reference numeral 10. The exemplary sock 10 is constructed on a circular hosiery knitting machine, and includes a plurality of yarns formed in needle and sinker loops extending in circumferential courses and axial wales. The sock 10 may be formed throughout of a body yarn and a ground yarn knitted in plated relationship in various stitch constructions described below, and with inlaid elastic yarns and pattern yarns in certain portions, areas, and regions of the sock.

Referring to FIGS. 3-6, the exemplary sock 10 comprises an integrally-knit raised ankle portion 11 and foot portion 12. The foot portion 12 includes an upper instep area 14, a lower sole area 15, and a reciprocally-knitted heel 16 and toe 17. The upper instep area 14 and lower sole area 15 are circularly-knit in foot portion 12 and designated by notional center lines ICL and OCL in FIGS. 3 and 5, such that an upper half of the foot portion 12 substantially defines the instep area 14 while the lower half substantially defines the sole area 15. The upper instep area 14 has a front ankle region 21, an intermediate instep region 22, and a forward instep region 23. These regions 21, 22, 23 are axially divided by notional center line TCL in FIG. 6. The lower sole area 15 has inner and outer arch regions 25, 26 axially divided by center line BCL in FIG. 4, and a forward ball region 27 adjacent the toe 17. The inner arch region 25 is designed to reside substantially adjacent an inner arch of the wearer's foot, as best shown in FIG. 2, and incorporates a generally semi-circular, anatomically-shaped targeted compression zone 30 comprising elastic yarns, pattern (or accent) yarns, and axially extending compression ridges 32, discussed further below. When applied to the foot, the compression zone 30 of sock 10 may exert an intensified targeted compression force at the inner arch of the foot which is substantially greater than the compression force applied in other directly adjacent areas of the foot portion 12. The intensified compression may be as much as 3-4 times greater (or more) in the compression zone 30 of the sock 10.

Figure 3:
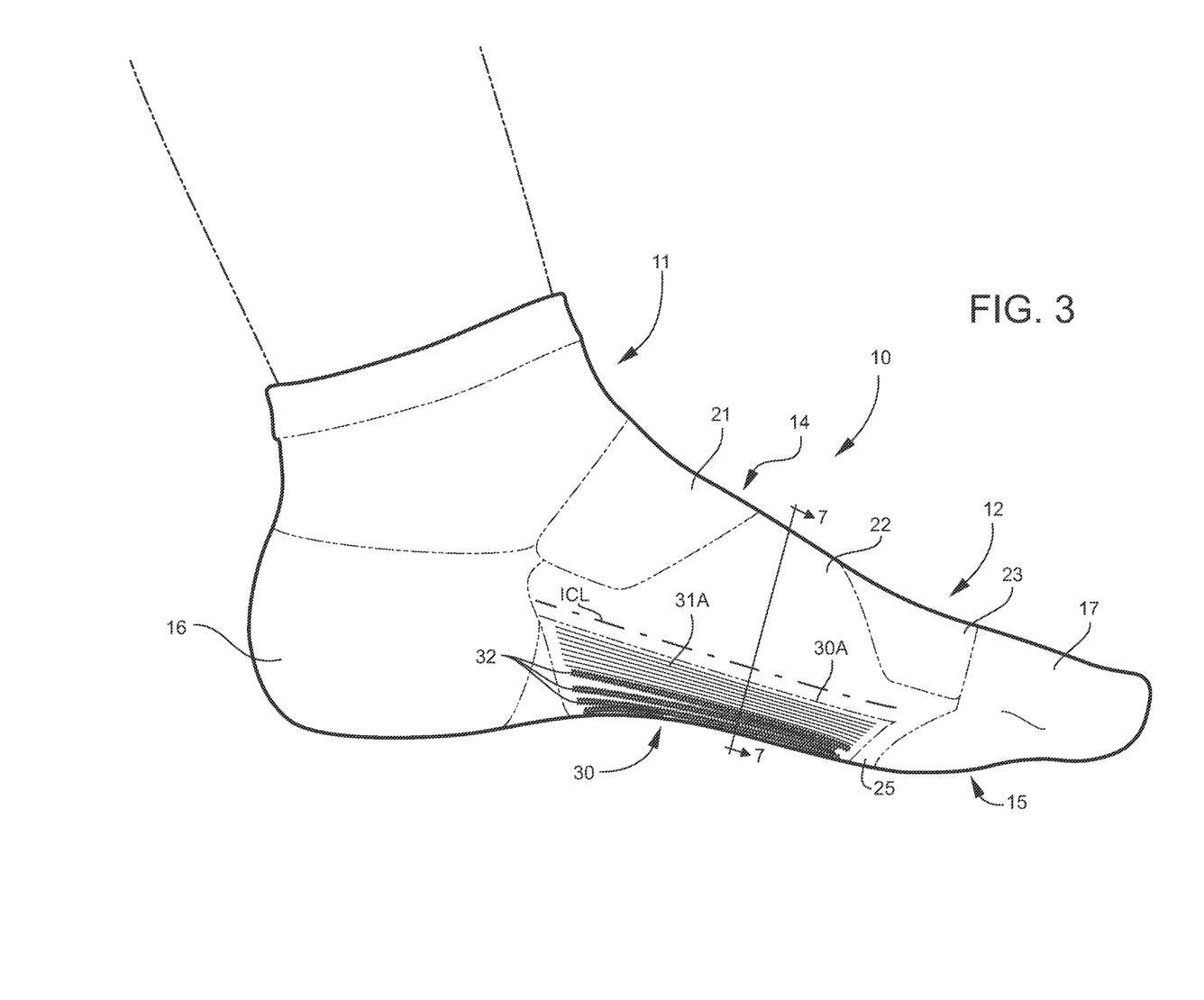
FIG. 3 is an inner arch side view of the exemplary sock.
Figure 4:
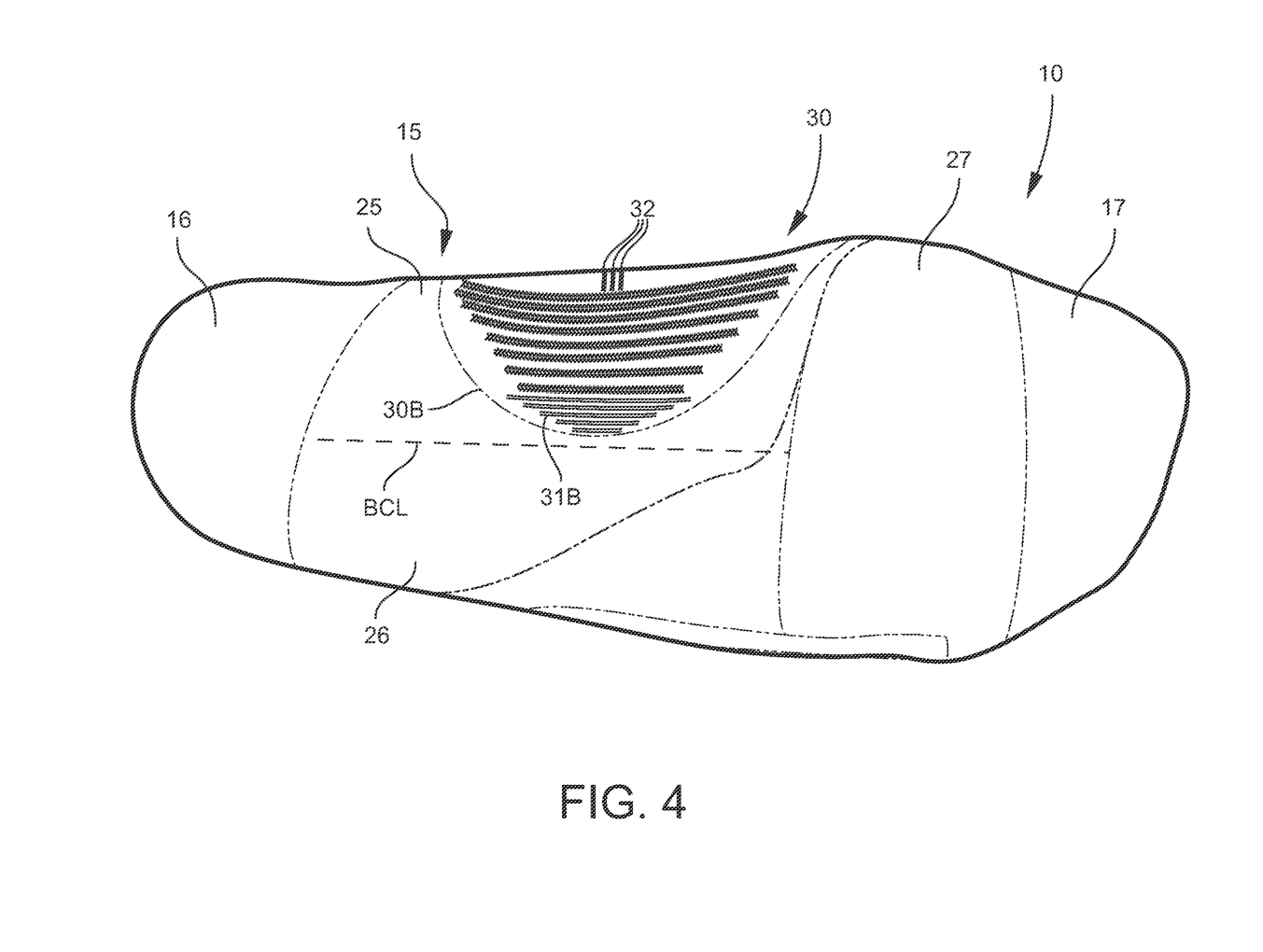
FIG. 4 is a bottom view of the exemplary sock.
Figure 5:
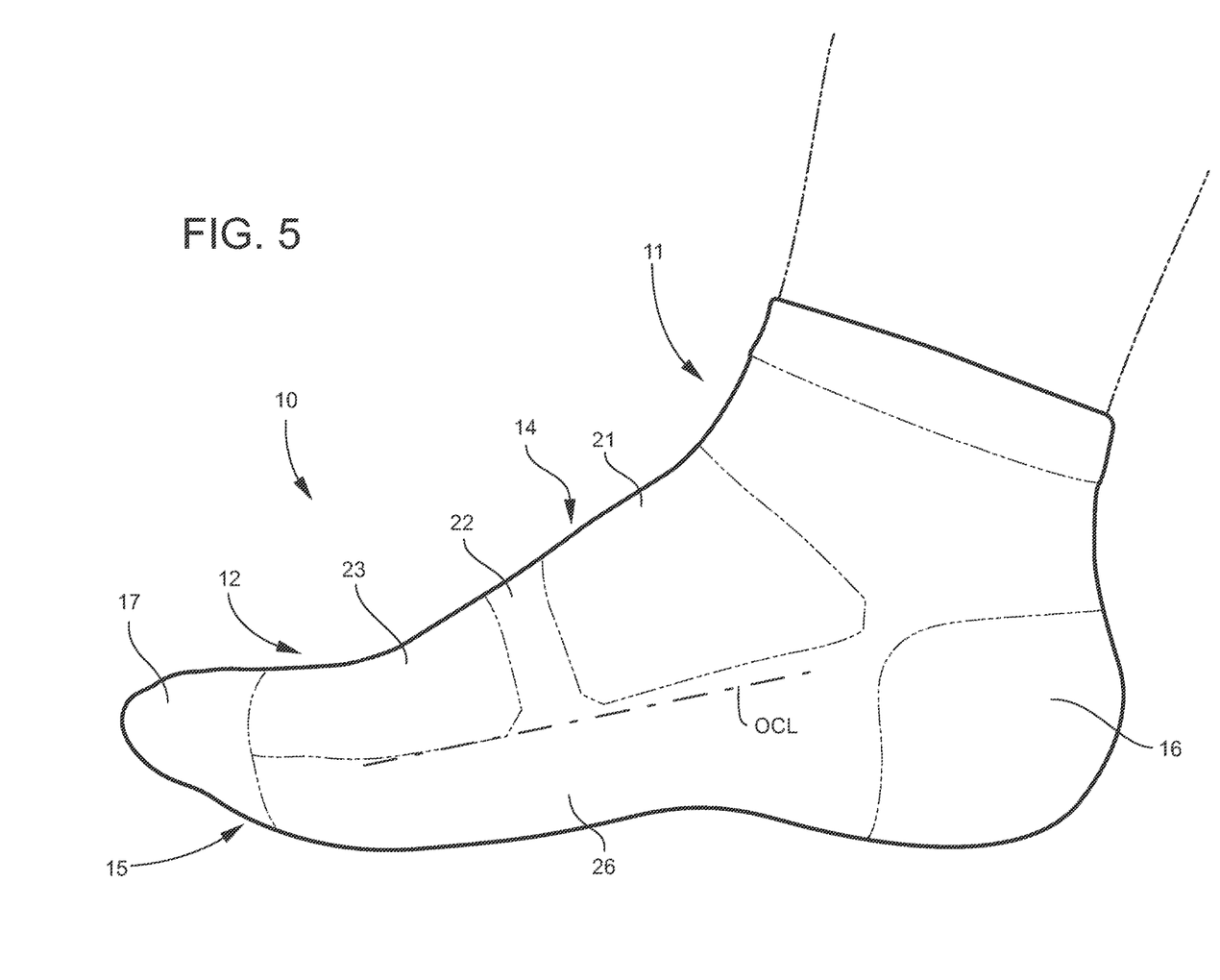
FIG. 5 is an outer arch side view of the exemplary sock.
Figure 6:
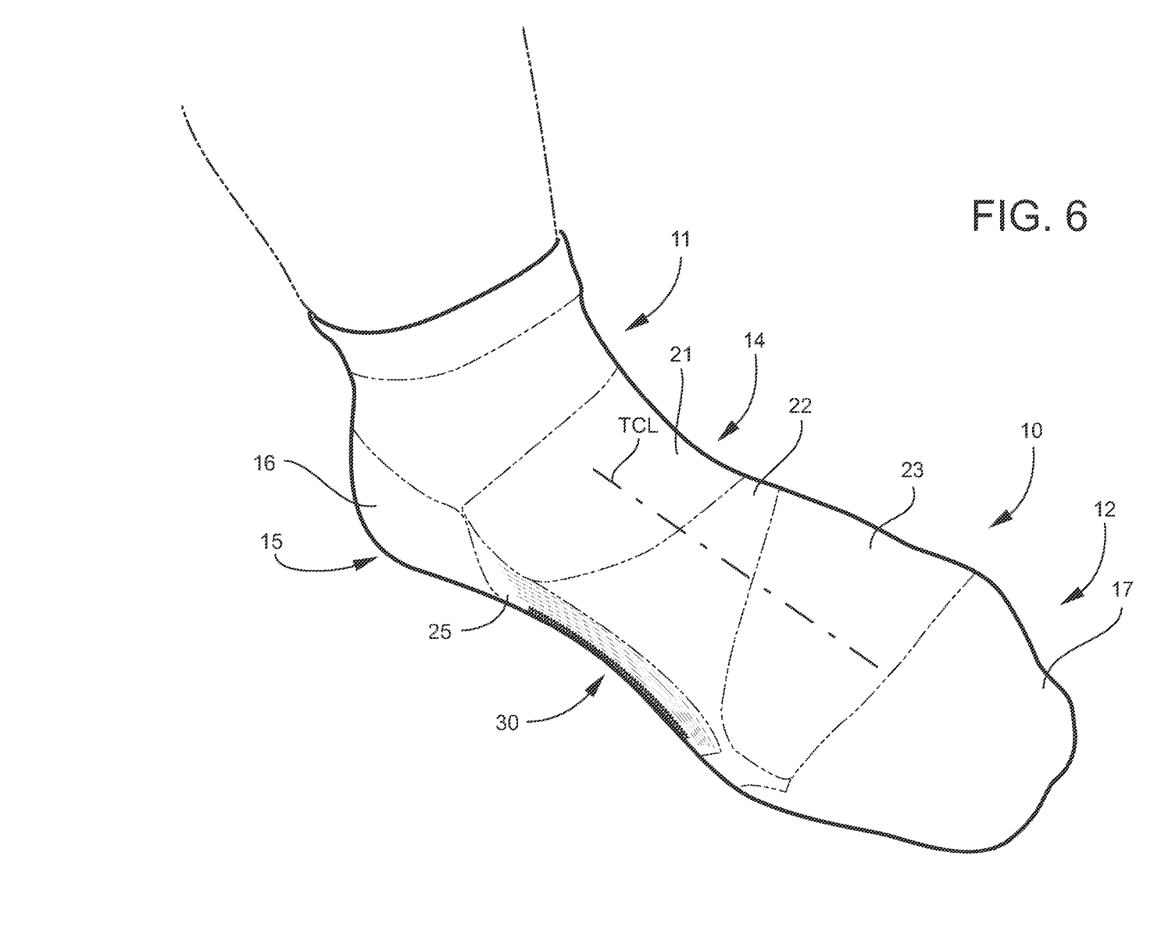
FIG. 6 is a top perspective view of the exemplary sock.
Figure 7:
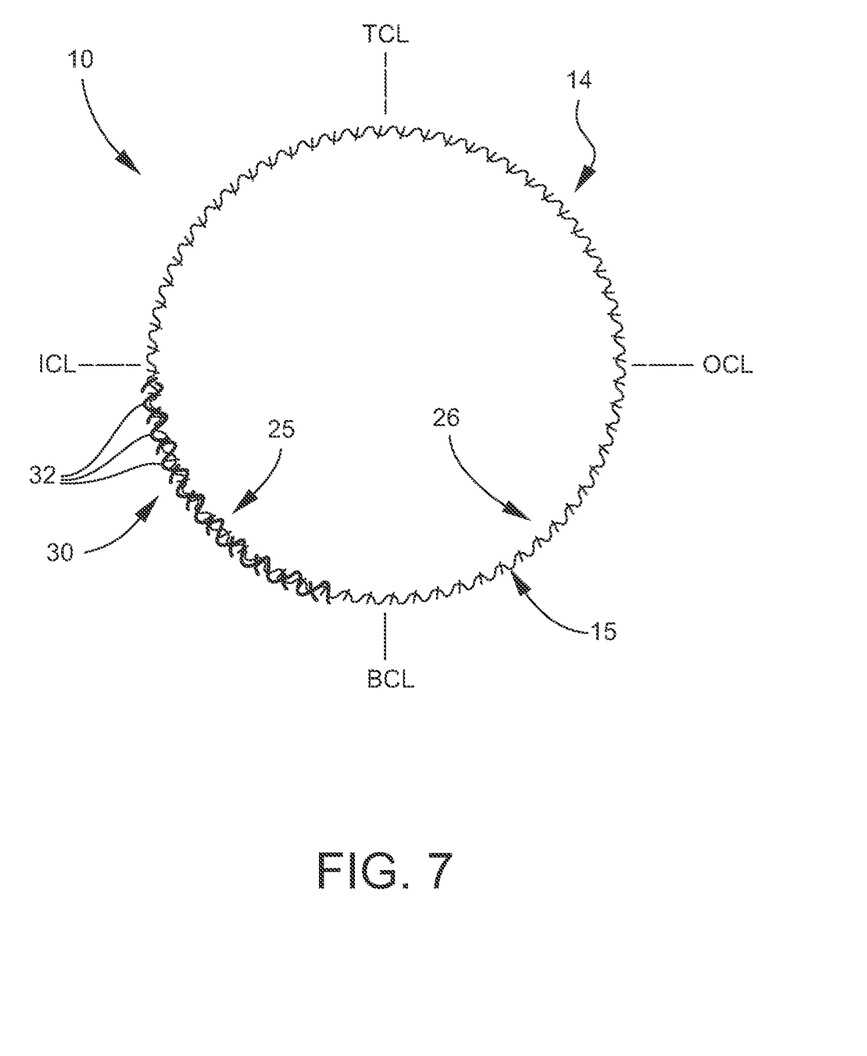
FIG. 7 is a cross-sectional view of the exemplary sock taken generally along line 7-7 of FIG. 3.

As best shown in FIGS. 3 and 4, the compression zone 30 has a substantially linear side 30A at its top margin 31A which extends adjacent the inside axial center line ICL of foot portion 12, and a substantially arcuate side 30B opposite the linear side 30A at its bottom margin 31B, and facing the bottom axial centerline BCL of the foot portion 12. FIG. 7 further illustrates quadrants of the circularly-knit foot portion 12 of sock 10. The quadrants are divided by respective center lines ICL, OCL, TCL, BCL discussed above. As shown, the targeted compression zone 30 may reside substantially entirely within the lower inside quadrant of the foot portion at the inner arch region 25 (substantially between ICL and BCL). The compression ridges 32 are spaced apart circumferentially from a top of the compression zone 30 to the bottom of the compression zone 30, and taper in axial length within a generally semi-circular shape between top and bottom margins 31A, 31B.

The remainder of the lower sole area 15 immediately surrounding the targeted compression zone 30 (both axially and circumferentially) comprises a less dense flat knit fabric structure with a one-by-one mock rib. The upper instep area 14 of the sock 10 may comprise a 1×1 mesh knit construction in the divided front ankle and forward instep regions 21, 23. The intermediate instep region 22 may incorporate a 1×1 mock rib construction similar to the fabric area immediately surrounding the compression zone 30. The heel and toe 16, 17 are formed in a conventional manner, and may also comprise mock ribbing. The ankle portion 11 of sock 10 may comprise a mesh knit elastic cuff, and mock ribbing knit in a conventional manner.

Exemplary Knit Structure of Compression Zone 30

Figure 8:
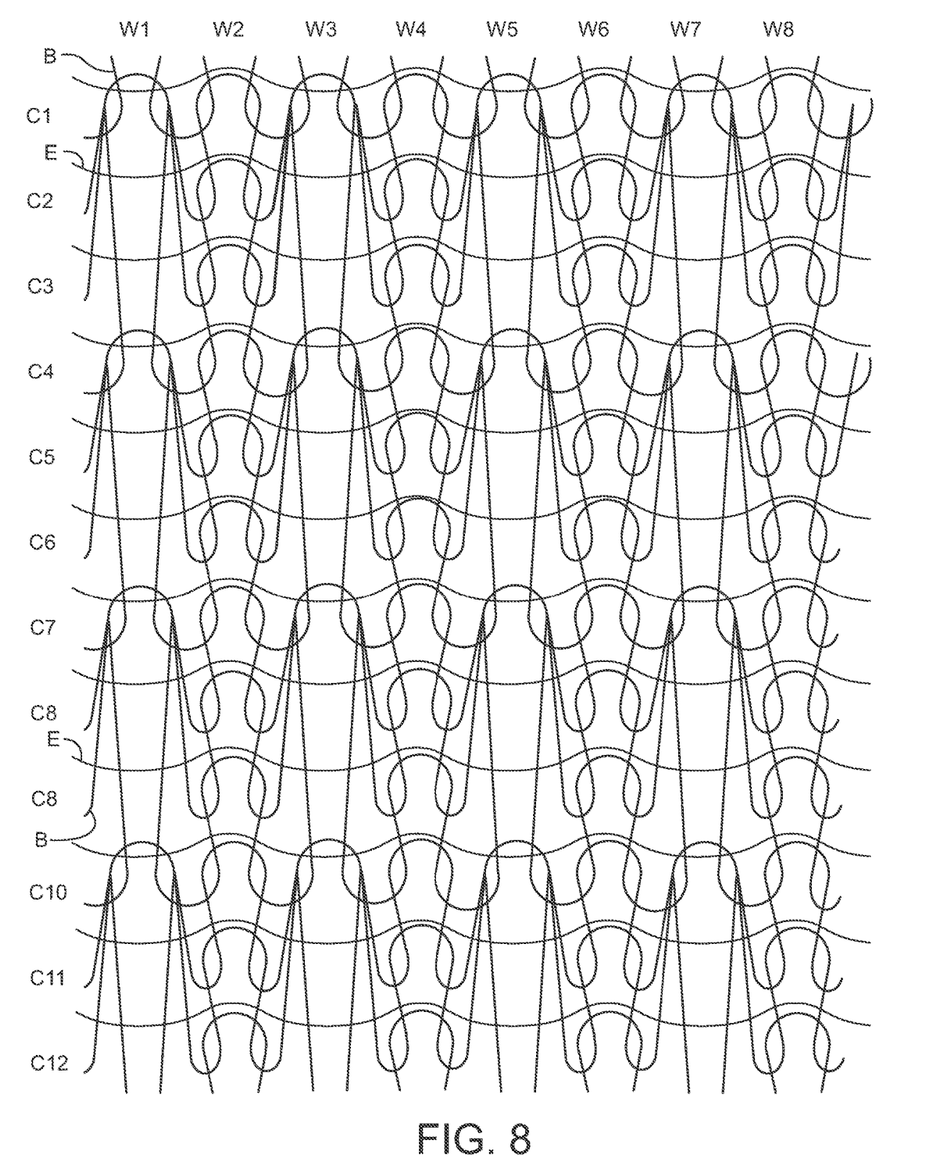
FIG. 8 illustrates an exemplary knit structure of top and bottom margins of the targeted compression zone.
Figure 9:
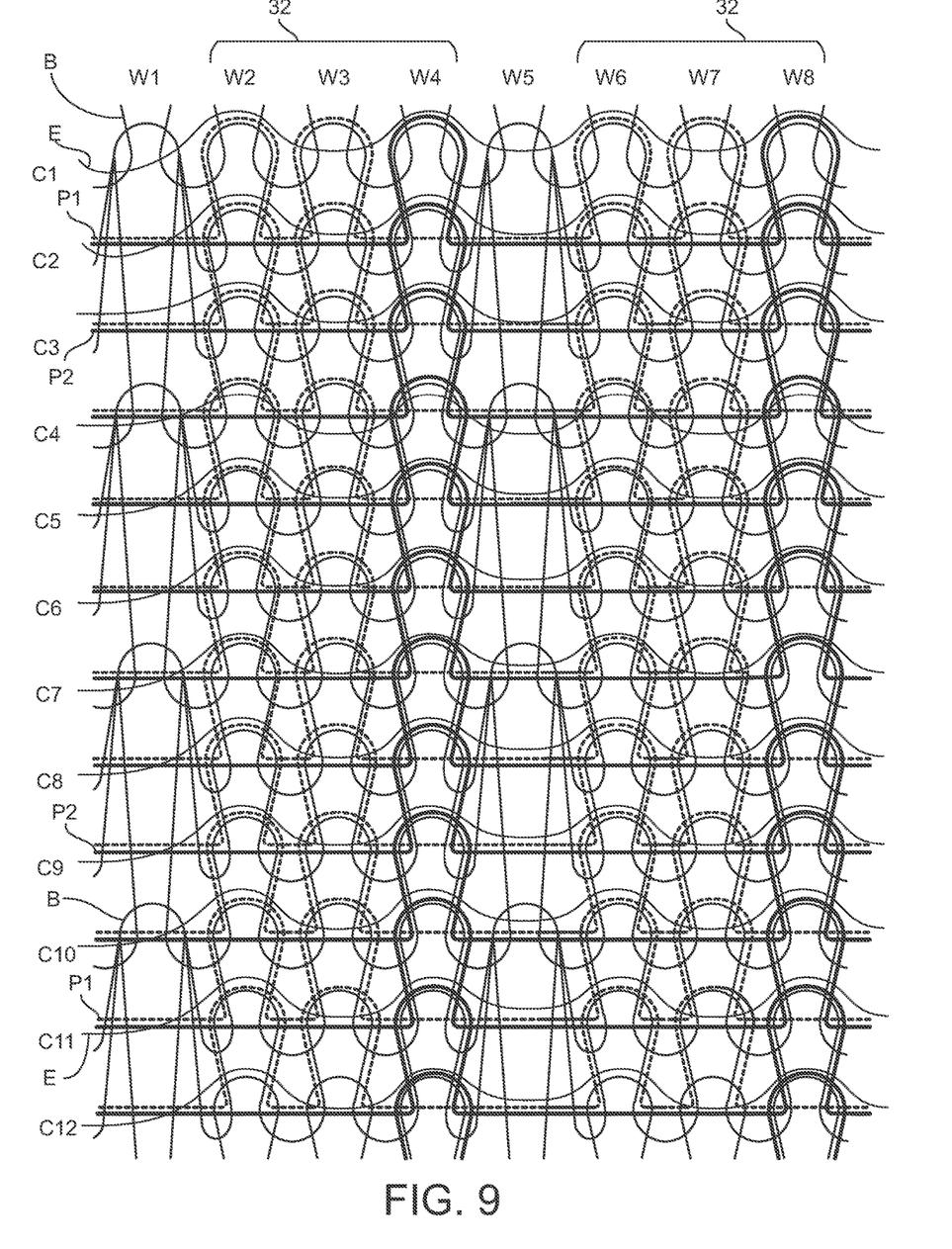
FIG. 9 illustrates an exemplary knit structure of the targeted compression zone between the top and bottom margins.

Referring to FIGS. 3, 4, 8, and 9, in the exemplary embodiment the targeted compression zone 30 of sock 10 is formed of a one-by-one mock rib construction with the elastic yarn (E) laid-in the plaited body yarn (B) on a reverse side of the fabric in each course C1-C12 by tuck and float stitches in needle loops of wales W1-W8. FIG. 8 illustrates the knit structure of the compression zone 30 in spaced top and bottom margins 31A, 31B—the compression zone 30, margins 31A, 31B, and axial compression ridges 32 being shown FIGS. 3 and 4. The axial compression ridges 32 between the margins 31A, 31B are formed by the introduction of two pattern yarns (P1) and (P2), shown in FIG. 9, integrally knit with the plaited body yarn (B) in each course C1-C12 in a manner using tuck and float stitches, such that the compression ridges 32 (W2-W4 and W6-W8) are raised and substantially more dense as compared to directly adjacent areas of the foot portion 12. For clarity of illustration, the pattern yarns (P1) and (P2) are distinguished in FIG. 9 by broken-lines and bold lines, respectively. In the exemplary embodiment, pattern yarn (P1) is knit in wales W2, W3, W6, and W7 of the plaited body yarn (B), and floats uncut across wales W1, W4, W5, and W8. Pattern yarn (P2) is knit in wales W4 and W8 of the plaited body yarn (B), and floats uncut across wales W1, W2, W3, W5, W6 and W7. As indicated previously, the compression zone 30 may be knit in a manner resulting in increased stitch density, tighter gauge, and reduced stretchability compared to directly adjacent areas of the foot portion 12.

For the purposes of describing and defining the present invention it is noted that the use of relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Exemplary embodiments of the present invention are described above. No element, act, or instruction used in this description should be construed as important, necessary, critical, or essential to the invention unless explicitly described as such. Although only a few of the exemplary embodiments have been described in detail herein, those skilled in the art will readily appreciate that many modifications are possible in these exemplary embodiments without materially departing from the novel teachings and advantages of this invention. Accordingly, all such modifications are intended to be included within the scope of this invention as defined in the appended claims.

In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Unless the exact language "means for" (performing a particular function or step) is recited in the claims, a construction under § 112, 6th paragraph is not intended. Additionally, it is not intended that the scope of patent protection afforded the present invention be defined by reading into any claim a limitation found herein that does not explicitly appear in the claim itself.

What is claimed:

1. A knit sock, comprising:
    a foot portion comprising a heel;
    a targeted compression zone formed with said sock, and comprising axially extending compression ridges spaced-apart from each other and extending axially from a first end of said compression zone proximate said heel to a second end of said compression zone, and wherein said compression ridges have different termination points at the second end of said compression zone, and wherein said targeted compression zone extends in a coursewise direction to occupy only a partial circumferential portion of said sock, thereby exerting an intensified targeted compression force at a predetermined point on a wearer while avoiding increased tightening circumferentially around the foot; and
    whereby the compression force applied by said sock within said targeted compression zone is greater than the compression force in directly adjacent areas of said sock.

2. The knit sock according to claim 1, wherein said targeted compression zone comprises elastic yarns laid-in said body yarn.

3. The knit sock according to claim 1, wherein said axially extending compression ridges comprise individual uncut pattern yarns.

4. The knit sock according to claim 1, wherein said targeted compression zone is semi-circular.

5. The knit sock according to claim 4, wherein a first side of said targeted compression zone is substantially arcuate, and wherein a second side of said targeted compression zone is substantially linear.

6. The knit sock according to claim 5, wherein said compression ridges taper in respective axial length from the linear side of said compression zone to the arcuate side of said compression zone.

7. The knit sock according to claim 6, wherein the arcuate side of said compression zone faces a bottom axial centerline of said foot portion.

8. The knit sock according to claim 7, wherein the linear side of said compression zone extends adjacent an inside axial centerline of said foot portion.

9. The knit sock according to claim 1, wherein said compression ridges shorten in respective axial lengths from the first end of said compression zone to the second end of said compression zone.

10. The knit sock according to claim 1, wherein said compression zone comprises double covered elastic yarns.

11. The knit sock according to claim 1, wherein said compression zone has an increased density as compared to directly adjacent areas of said sock.

12. The knit sock according to claim 1, wherein said targeted compression zone has reduced coursewise and walewise stretchability relative to directly adjacent areas of said sock.

13. A knit sock integrally knit of a body yarn in circumferential courses and axial wales, and comprising:
    a foot portion and an ankle portion, said foot portion comprising a heel;
    a targeted compression zone formed with said sock, and comprising axially extending compression ridges spaced-apart from each other and extending axially from a first end of said compression zone proximate said heel to a second end of said compression zone, and wherein said compression ridges have different termination points at the second end of said compression zone, and wherein said targeted compression zone extends in a coursewise direction to occupy only a partial circumferential portion of said sock, thereby exerting an intensified targeted compression force at a predetermined point on a wearer while avoiding increased tightening circumferentially around the foot; and
    each axial compression ridge comprising at least one pattern yarn knit with the body yarn using tuck and float stitches such that said compression ridges are raised and more dense as compared to directly adjacent areas of said sock, whereby the compression force applied by said sock within said targeted compression zone is greater than the compression force in directly adjacent areas of said sock.

* * * * *